United States Patent
Rogel-Castillo et al.

(10) Patent No.: US 10,712,326 B2
(45) Date of Patent: Jul. 14, 2020

(54) NONDESTRUCTIVE METHOD OF IDENTIFYING CONCEALED DAMAGE IN NUTS

(71) Applicant: The Regents of the University of California, Oakland, CA (US)

(72) Inventors: Cristian Rogel-Castillo, Davis, CA (US); Alyson Mitchell, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/817,238

(22) Filed: Nov. 19, 2017

(65) Prior Publication Data
US 2018/0313804 A1     Nov. 1, 2018

Related U.S. Application Data

(60) Provisional application No. 62/426,514, filed on Nov. 26, 2016.

(51) Int. Cl.
| | | |
|---|---|---|
| *G01N 21/84* | (2006.01) | |
| *G01N 33/02* | (2006.01) | |
| *G01N 21/95* | (2006.01) | |
| *G01N 21/3563* | (2014.01) | |
| *G01N 21/359* | (2014.01) | |

(52) U.S. Cl.
CPC ......... *G01N 33/025* (2013.01); *G01N 21/359* (2013.01); *G01N 21/3563* (2013.01); *G01N 21/95* (2013.01); *G01N 2021/8405* (2013.01); *G01N 2021/8466* (2013.01); *G01N 2201/10* (2013.01); *G01N 2201/129* (2013.01)

(58) Field of Classification Search
CPC .. G01N 33/025; G01N 21/95; G01N 21/3563; G01N 21/359
See application file for complete search history.

(56) References Cited

U.S. PATENT DOCUMENTS

| | | | | |
|---|---|---|---|---|
| 5,345,081 A * | 9/1994 | Rogers | ................. | G01N 33/025 250/223 R |
| 6,037,591 A * | 3/2000 | Neri | .................... | G01N 21/8806 250/223 B |
| 6,873,680 B2 * | 3/2005 | Jones | ..................... | G01N 23/18 250/341.8 |
| 8,933,405 B2 * | 1/2015 | Diamond | ........... | G01N 21/4795 250/339.07 |
| 9,201,006 B2 * | 12/2015 | Diamond | ............. | A61B 5/0059 |

(Continued)

OTHER PUBLICATIONS

Canneddu et al. Quality Evaluation of Shelled and Unshelled Macadamia Nuts by Means of Near-Infrared Spectroscopy (NIR). Journal of Food Science vol. 81, Nr 7, May 2016, pp. 1613-1621 (Year: 2016).*

(Continued)

*Primary Examiner* — David P Porta
*Assistant Examiner* — Djura Malevic
(74) *Attorney, Agent, or Firm* — Kilpatrick Townsend and Stockton LLP (57) ABSTRACT

Provided are methods and systems for efficiently and non-invasively identifying nuts (e.g., almonds) having concealed damage using near infrared scanning. The methods identify nuts having concealed damage with a certainty greater than 90% and an error rate that is less than 10%.

19 Claims, 5 Drawing Sheets

(56) References Cited

U.S. PATENT DOCUMENTS

| 9,395,346 B2* | 7/2016 | Walukas | G01N 21/59 |
| 2006/0064780 A1* | 3/2006 | Munck | A01H 5/10 |
| | | | 800/284 |

OTHER PUBLICATIONS

Atungulu et al. Infrared Pre-Drying and Dry-Dehulling of Walnuts for Improved Processing Efficiency and Product Quality, Applied Engineering in Agriculture, (2013) vol. 29(6) pp. 961-971 (Year: 2013).*

Borras, E. et al.; "Fast and robust discrimination of almonds (*Prunus amygdalus*) with respect to their bitterness by using near infrared and partial least squares-discriminant analysis"; *Food Chemistry*; vol. 153; 2014; pp. 15-19.

Pearson, T.C.; "Use of Near Infrared Transmittance to Automatically Detect Almonds with Concealed Damage"; *Lebensm.-Wiss.u.-Technol.*; vol. 32; 1999; pp. 73-78.

Rogel-Castillo, C.et al.; "Use of near-infrared spectroscopy and chemometrics for the non-destructive identification of concealed damage in raw almonds (*Prunus dulcis*)"; *J. Agric. Food Chem.*; Jun. 16, 2016; 25 pages.

* cited by examiner

NONDESTRUCTIVE METHOD OF IDENTIFYING CONCEALED DAMAGE IN NUTS

CROSS-REFERENCE TO RELATED APPLICATIONS

This application claims the benefit under 35 U.S.C. § 119(e) of U.S. Provisional Application No. 62/426,514, filed on Nov. 26, 2016, which is hereby incorporated herein by reference in its entirety for all purposes.

BACKGROUND

Figure 1:
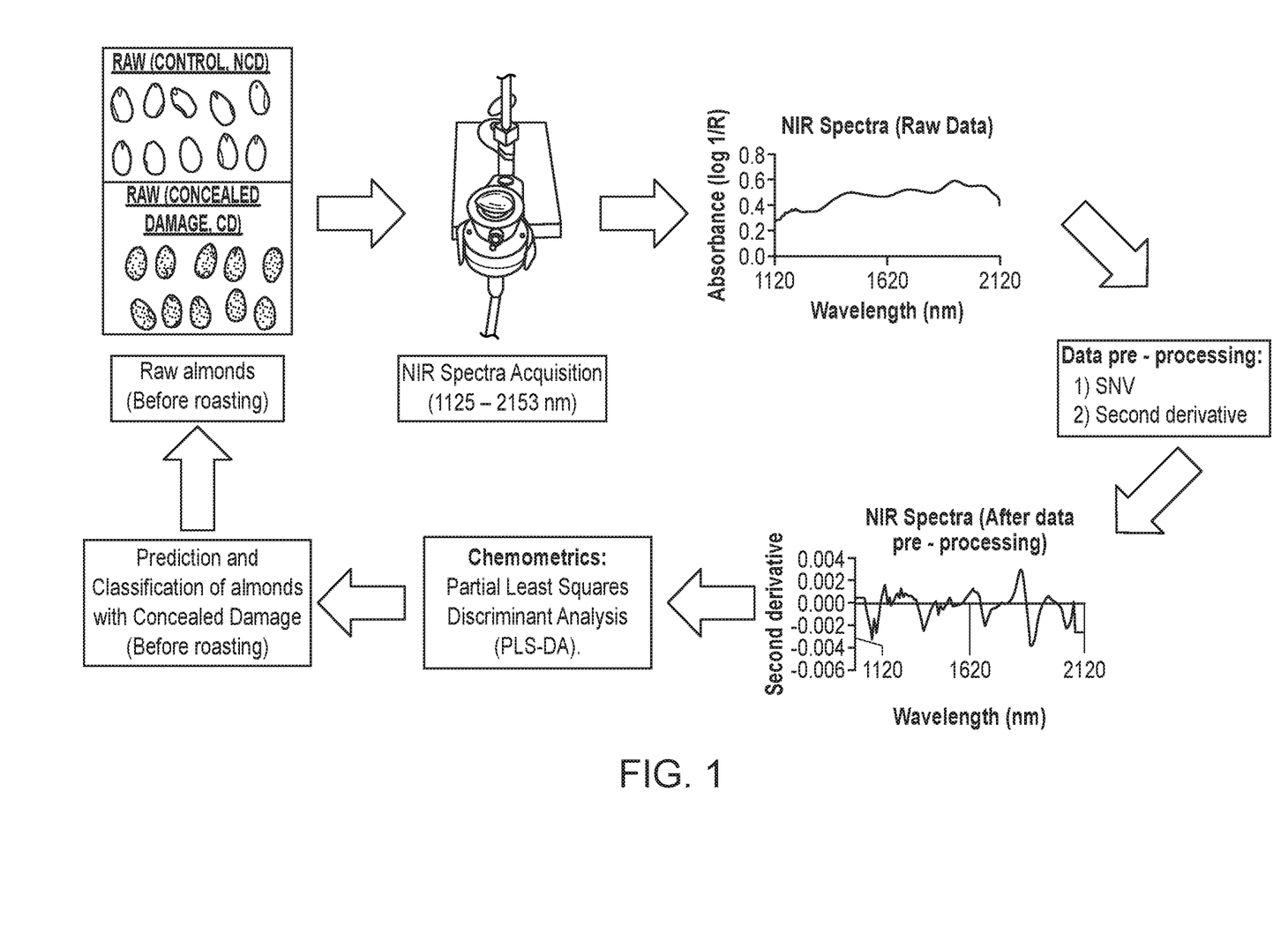
FIG. 1 illustrate a flow chart of an embodiment of the methods described herein.
Figure 2:
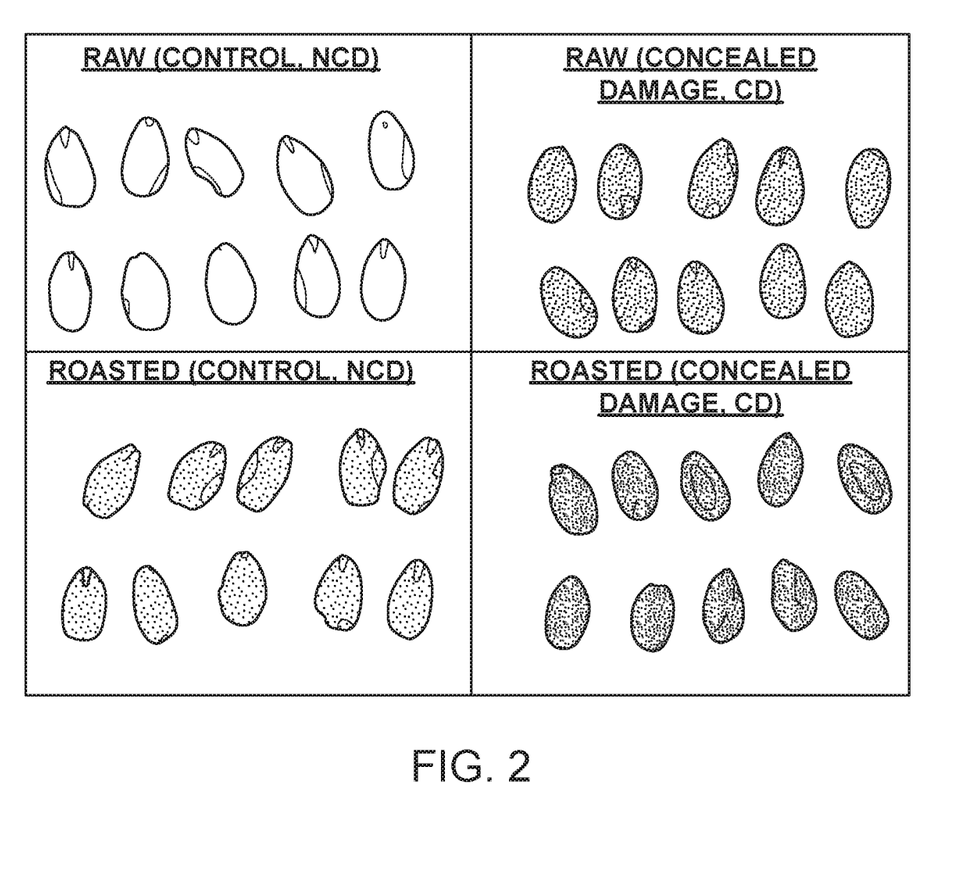
FIG. 2 illustrates color development in raw and roasted almonds (120° C. for 90 min) exposed to 5% moisture (control) and 11% moisture (concealed damage).

Concealed damage (CD) in raw almonds (*Prunus dulcis* (Mill.) D. A. Webb) is defined by the industry as a brown discoloration of the kernel interior (nutmeat) that appears only after moderate to high heat treatment (e.g. blanching, drying, roasting, etc.) as shown in FIG. 1. CD may develop anytime during harvest when rain occurs, or after harvest when kernels are in windrows or stockpiles and exposed to warm and moist environments (1,2). Raw almond kernels with CD, have no visible defects on the interior or exterior surface of the kernel. Additionally, there are no visible signs of CD on the surface of whole roasted kernels (3). CD is frequently associated with a strong bitter flavor(s) that can result in immediate consumer rejection (1). Currently there are no screening methods available for detecting CD in raw almonds, or other nuts affected by CD, and processors often do not realize nuts are damaged until after they have been roasted (1). Under current production practices, the most common methods for detecting CD involve visual inspection of roasted almonds after they are split open. Kernels with a "dark brown" color over ~50% of the interior of the kernel are considered to have CD (4). A similar approach is used for hazelnuts (5). Visual inspection and manual sorting is time-consuming, subjective, labor intensive and cannot be used to identify nuts with CD before heat treatments. This can result in significant product loss.

The current hypothesis is that the browning associated with CD is related to the Maillard reaction. Moisture can induced the hydrolysis of carbohydrates and potential availability of reducing sugars for Maillard browning reactions. For example, in macadamia nuts exposed to moisture during harvesting, increased levels of reducing sugars were observed in nuts with internal browning (6). Similar observations were made in hazelnuts (7) and in almonds exposed to simulated rainfall (2). In more recent studies, elevated levels of volatiles related to lipid oxidation and amino acid degradation were observed in almonds with CD (8). Both lipid oxidation products and protein degradation products can serve as reactants in the Maillard browning reaction.

Near-infrared spectroscopy (NIR) is a rapid and effective method for screening foods for specific chemical and physical characteristics (9). NIR is advantageous as a screening method as it is non-destructive, can be used on whole foods, and produces no waste. The NIR spectral region (720 to 2500 nm) is ideally suited for foods as it contains absorbance bands that result primarily from three chemical bonds: C—H (fats, oil, hydrocarbons), O—H (water, alcohol) and N—H (protein). NIR spectroscopy is increasingly considered one of the more promising in-line detection methods for rapidly measuring specific chemical properties of food.6 It has been successfully applied in detecting quality defects in macadamia kernels (7), walnuts (10), chestnuts (11-12), hazelnuts (13-14), and soybean seed (15). It has also been employed for food composition analysis including oleic and linoleic acid content in peanut seed (16), acidity and water content in hazelnuts (17), and characterization of shea tree nut fat profiles (18).

Pearson (1999) was the first to recognize the use of NIR spectroscopy for the identification of CD in raw almonds (4, 19) and evaluated the transmission spectrum from 700-1400 nm in almonds soaked in water, and dried but not roasted. In these studies, almonds were either soaked for 30 minutes and exposed to 95% relative humidity for 30 hours (short moisture), or soaked for 60 minutes and exposed to 95% relative humidity for 60 hours (long moisture). Almonds were then dried at either 55 or 110° C. The higher temperature and shorter soak times produced the greatest amount of CD. Almonds with CD had enhanced absorption at 930 nm (oil absorption band). Raw almonds with CD could be distinguished from normal almonds at an error of 12.4% by using principal components of the absorbance, first derivative and second derivative spectra between 1000-1300 nm. Pearson (1999) recognized that collecting the NIR spectra over the full transmission range would be too slow to achieve desired inspection rates of 40 nuts/s and therefore tested the feasibility of using just 6 light emitting diodes at 660, 830, 880, 890, 940, and 950 nm (19). These data resulted in a classification error rate of 14.3% for the validation set. More recently, Nakariyakul (20-21) achieve a higher classification rate using hyperspectral transmission and focusing on a sub-set of absorbing bands (760, 920, 935, and 970 nm) with a false negative error rate of 14.81%. Almonds used in this study were generated by Pearson (1999) as described above.

SUMMARY

In one aspect, provided are methods of identifying a nut having concealed damage. In some embodiments, the methods comprise the steps of:

a) obtaining Near-Infrared Spectroscopy (NIR) diffuse reflectance spectra between 1125-2153 nm of a dehulled whole raw nut;

b) converting the NIR reflectance spectra to NIR absorbance spectra;

c) evaluating the NIR absorbance spectra within the wavelength ranges of 1408-1462 nm, 1692-1740 nm, 1902-1959 nm and 2064-2104 nm;

d) performing partial least square discriminant analysis (PLS-DA) within the wavelength ranges of step c) and assigning a PLS-DA value; and e) identifying the nut as having concealed damage when the PLS-DA value is above a threshold value. In varying embodiments, the NIR absorbance spectra are subject to Standard Normal Variate (SNV) preprocessing. In varying embodiments, the NIR absorbance spectra are subject to second order Savitzky-Golay filter or second derivative preprocessing. In varying embodiments, the NIR absorbance spectra are subject to a combination of (i) second order Savitzky-Golay filter or second derivative preprocessing and (ii) Standard Normal Variate (SNV) preprocessing. In varying embodiments, the pre-processing employs a 9-point second order Savitzky-Golay filter.

In a related aspect, provided are methods of identifying a nut having concealed damage. In varying embodiments, the methods comprise the steps of:

a) obtaining Near-Infrared Spectroscopy (NIR) diffuse reflectance spectra between 1125-2153 nm of a dehulled whole raw nut;

b) converting the NIR reflectance spectra to NIR absorbance spectra;

c) evaluating the NIR absorbance spectra within the wavelength ranges of 1392-1546 nm, 1692-1781 nm, and 1902-1991 nm;

d) performing partial least square discriminant analysis (PLS-DA) within the wavelength ranges of step c) and assigning a PLS-DA value; and e) identifying the nut as having concealed damage when the PLS-DA value is above a threshold value. In some embodiments, the NIR absorbance spectra are subject to (i) smoothing preprocessing and (ii) second order Savitzky-Golay filter or second derivative preprocessing. In varying embodiments, the pre-processing employs a 15-point second order Savitzky-Golay filter.

With respect to further embodiments of the methods, in varying embodiments, the converting step (b) employs log (1/R) transformation. In some embodiments, the nut is selected from a true nut, a drupe seed, a nut-like gymnosperm seed, and a nut-like angiosperm seed. In varying embodiments, the nut is edible by a human. In varying embodiments, the nut is selected from the group consisting of almonds, pistachios, pecans, walnuts, shea nuts, macadamia nuts, hazel nuts, peanuts, cashews, walnuts, chestnuts, pine nuts and brazil nuts. In varying embodiments, the nut is an almond. In varying embodiments, the converting step employs a 9-, 11-, 13- or 15-point second order Savitzky-Golay filter. In varying embodiments, the threshold value is 0.5 (e.g., arbitrary units). In varying embodiments, one or more steps of the method are automated. In varying embodiments, the method is high throughput. In some embodiments, the methods further comprise the step f) of separating nuts identified as having concealed damage from nuts identified as not having concealed damage. In varying embodiments, one or more (e.g., 2, 3, 4, 5) of steps a) to f) are performed or implemented by a computer. In varying embodiments, the whole raw nut is not purposefully breached, split or damaged. In varying embodiments, the whole raw nut is not subject to a heat treatment. In varying embodiments, the nut is not subject to heat treatment, blanched, or roasted. In varying embodiments, for each spectrum, 30-1000 scans with an integration time of 550-2500 µs are averaged. In varying embodiments, for each spectrum, 1000 scans with an integration time of 550 µs are averaged. In varying embodiments, for each spectrum, 30 scans with an integration time of 2500 µs are averaged. In varying embodiments, the method has an overall error rate of less than about 10%, e.g., less than about 9%, less than about 8%, and a false negative error rate of less than about 20%, e.g., less than about 19%, 18%, 17%, 16% or 15%. In varying embodiments, the method identifies nuts having concealed damage with greater than 90% certainty, e.g., greater than 91% or 92% certainty.

In another aspect, provided is a system for identifying a nut having concealed damage. In some embodiments, the system comprises:

(i) a conveyor belt;

(ii) one or more near infrared (NIR) scanners downstream of a loading point on the conveyor belt and in mechanical communication with the conveyor belt, wherein the one or more NIR scanners are positioned above the conveyor belt and at a proximity and angle to the conveyor belt such that the NIR scanner can scan nuts placed on the conveyor belt;

(iii) a computer in communication (e.g., electrical, wireless) with the one or more NIR scanners, wherein the computer is capable of performing or implementing one or more (e.g., 2, 3, 4, 5) steps in the methods described above and herein;

(iv) a deflector in communication with the computer, and optionally the one or more NIR scanners, wherein the deflector separates nuts identified as having concealed damage from undamaged nuts. In some embodiments, the one or more NIR scanners are capable of scanning at least 40 nuts per second.

In a related aspect, provided is a system for identifying a nut having concealed damage, the system comprising:

(i) a stationary platform;

(ii) a movable element attached to a near infrared (NIR) scanner positioned above the stationary platform, wherein the NIR scanner is positioned at a proximity and angle to the platform such that the NIR scanner can scan nuts placed on the platform; and (iii) a computer in communication with the NIR scanner, wherein the computer is capable of performing or implementing one or more steps in the methods described above and herein.

DETAILED DESCRIPTION

1. Introduction

Concealed damage (CD) is defined as a brown discoloration of the kernel interior (nutmeat) that appears only after moderate to high heat treatment (e.g. blanching, drying, roasting, etc.). Raw almonds with CD have no visible defects before heat treatment. Currently there are no screening methods available for detecting CD in raw almonds.

Herein, we present the development of a prediction model for the classification of almonds with CD using reflectance NIR in the extended range of the NIR spectrum (1125-2153 nm) and by employing data pre-processing and partial least square discriminant analysis (PLS-DA). Almonds evaluated in this study were exposed to controlled humidity environments that produced an internal nut moisture content of ~5% (control), 8% (mild CD) and 11% (100% CD). The percent CD in the raw almonds was validated using colorimetry as described previously (8). Almond kernels with CD have less NIR absorbance in the region related with oil, protein and carbohydrates. Using partial least square regression and discriminant analysis (PLS-DA) and by selecting specific wavelengths, three classification models were developed. The calibration models have false positive and false negative error rates ranging between 12.4-16.1% and 10.6-17.2%, respectively. The percent error rates ranged between 8.2-9.2%. Second derivative pre-processing of selected wavelength resulted in the most robust predictive model.

Developing a rapid in-line screening method for detecting CD in raw almonds is a step towards improving quality control measures in almond processing and offers the advantage of sorting almonds with CD into product lines that do not require roasting or other heat treatments.

2. Non-Destructive Methods of Identifying Concealed Damage Nuts

Provided are methods of identifying a nut having concealed damage. The methods find use for the non-destructive detection of concealed damage in true nuts, drupe seeds, nut-like gymnosperm seeds, and nut-like angiosperm seeds. The methods are applicable to non-destructively detecting concealed damage in almonds, pistachios, pecans, walnuts, shea nuts, macadamia nuts, hazel nuts, peanuts, cashews, walnuts, chestnuts, pine nuts and brazil nuts. The present methods allow for the determination of concealed damage in nuts without the purposeful destruction or damage to the nut or shell. Generally, in performing the present methods, the nut need not be purposefully breached, split or damaged. Further the nut need not be subject to a heat treatment, blanched, or roasted. In certain embodiments, the nuts are dried or humidified so that the internal kernels have an internal moisture content appropriate for storage, e.g., in the range of about 5 wt. % to about 10 wt. %, e.g., from about 5 wt. % to about 6 wt %, 7 wt. %, 8 wt. %, 9 wt. %. Generally, the methods have an overall error rate of less than 10%, can identify nuts having concealed damage with a certainty of at least 90%, with a specificity of greater than 85% and a selectivity of greater than 80%.

a. Obtaining Near-Infrared Spectroscopy (NIR) Diffuse Reflectance Spectra in a Spectral Range from 1125-2153 nm Nuts are obtained and, in varying embodiments, stored under controlled humidity conditions such that sufficient levels of kernel moisture are maintained. As appropriate, the nuts can be stored under conditions producing an internal kernel moisture in the range of about 5 wt. % to about 10 wt. %, e.g., from about 5 wt. % to about 6 wt %, 7 wt. %, 8 wt. %, 9 wt. %, as validated using methods known in the art, e.g., gravimetrically of dried samples.

NIR diffuse reflectance spectra can be obtained using methods known in the art, e.g., using an NIR spectrometer capable of collecting diffuse reflectance spectra in a spectral range from 1125-2153 nm. NIR spectrometers are commercially available and those capable of collecting diffuse reflectance spectra in a spectral range from 1125-2153 nm can find use. Illustrative NIR spectrometers that can be used in the present methods include without limitation, e.g., JDSU MicroNIR™ 2200 Spectrometer from Viavi (viavisolutions.com); Antaris MX FT-NIR Process Analyzer from Thermo Fisher Scientific (thermofisher.com); Bomen FT-NIR MB160PH Aridzone spectrometer (triadscientific.com); MB3600 FT-NIR Analyzer and other NIR analyzers from ABB Analytical (abb.com/analytical); NIRMaster Pro FT-NIR Spectrometer and other NIH spectrometers from BUCHI Corporation (buchi.com), as well as NIR spectrometers from Horiba Scientific (horiba.com).

In varying embodiments, for each spectrum, 30-1000 scans with an integration time of 550-2500 µs are averaged. In general, the higher the number of scans, the lower the averaged integration time. Conversely, the lower the number of scans, the higher the averaged integration time. In varying embodiments, 1000 scans with an integration time of 550 µs are averaged. In varying embodiments, 30 scans with an integration time of 2500 µs are averaged.

In varying embodiments, the step of obtaining n NIR diffuse reflectance spectra is performed by or implemented by a computer, e.g., in certain embodiments, the NIR spectrometer can be controlled by or directed by a computer. In varying embodiments, the obtained NIR diffuse reflectance spectra is stored on a computer-readable tangible medium, e.g., a computer hard drive, a flash drive, a CD.

b. Converting the NIR Reflectance Spectra to NIR Absorbance Spectra

The obtained NIR reflectance spectra are converted to NIR absorbance spectra and then subject to data pre-processing. In varying embodiments, NIR reflectance spectra are converted to NIR absorbance spectra employing a log (1/R) transformation. In certain embodiments, the NIR reflectance spectra are compared to a white calibration reference as a control.

The absorbance spectra are subject to mathematical pre-preprocessing. Any of a number of different pre-processing techniques can be employed, and pre-processing of the NIR reflectance spectra can be performed or implemented by a computer using commercially available software. In varying embodiments, the pre-processing method applied is smoothing, standard normal variate (SNV), second order Savitzky-Golay filter (second derivative preprocessing) or a combination of two or more of smoothing, standard normal variate (SNV) and second order Savitzky-Golay filter (second derivative preprocessing). In varying embodiments, the pre-processing method applied is a combination of smoothing and second order Savitzky-Golay filter (second derivative preprocessing). Those of skill in the art will recognize that a suitable data pretreatment depends on the data to be analyzed (many measurements of a particular sample). Out of a number of tested pretreatments, the preferred pretreatment is characterized by the lowest statistical errors obtained in the data analysis step (linear regression). See, Metrohm NIRSystem. Herisau, Switzerland. Monograph: NIR Spectroscopy A guide to near-infrared spectroscopic analysis of industrial manufacturing processes. Found at metrohmsiam.com/processtalk/PT_04/PT04_MEP_Monograph_NIRS_81085026EN.pdf.

The second order Savitzky-Golay filter (second derivative preprocessing) can be within the range of 9 to 15 points, depending on the desired or needed resolution. In varying embodiments, the filter for second order Savitzky-Golay pre-processing is set at 9-, 11-, 13- or 15-points. Commercially available software of use for pre-processing NIR absorbance spectra include without limitation, e.g., R and R-Studio (rstudio.com), as described herein, R-Project (rproject.org), Matlab (mathworks.com), Octave (gnu.org) and NIR Calibration Model (calibrationmodel.com). R and R-studio+ and Matlab are commonly used software for pre-processing NIR absorbance spectra. However, any statistical package capable of performing chemometrics analysis would be suitable. Other or additional pre-processing methods may be applied, including, e.g., localized standard normal variate (SNV) (Bi, et al., *Anal Chim Acta.* 2016 Feb. 25; 909:30-40).

c. Evaluating the NIR Absorbance Spectra

In varying embodiments, the converted and pre-processed NIR absorbance spectra is evaluated within the wavelength ranges of 1408-1462 nm, 1692-1740 nm, 1902-1959 nm and 2064-2104 nm. In varying embodiments, the converted NIR absorbance spectra is evaluated within the wavelength ranges of 1392-1546 nm, 1692-1781 nm, and 1902-1991 nm.

In certain embodiments, the wavelengths of the NIR absorbance spectra to be evaluated is determined by the pre-processing method applied for conversion of NIR reflectance spectra to NIR absorbance spectra. For example, in certain embodiments, when the pre-processing method applied is standard normal variate (SNV), second order Savitzky-Golay filter (second derivative preprocessing) or a combination of standard normal variate (SNV) and second order Savitzky-Golay filter (second derivative preprocessing), the converted NIR absorbance spectra is evaluated within the wavelength ranges of 1408-1462 nm, 1692-1740 nm, 1902-1959 nm and 2064-2104 nm. In certain embodiments, when the pre-processing method applied is a combination of smoothing and second order Savitzky-Golay filter (second derivative preprocessing), the converted NIR absorbance spectra is evaluated within the wavelength ranges of 1392-1546 nm, 1692-1781 nm, and 1902-1991 nm.

d. Performing Partial Least Square Discriminant Analysis (PLS-DA)

In the present methods and systems, PLS-DA can be performed using the absorbance (after processing) at the maximum of the peak. Execution of PLS-DA of NIR spectra is known in the art can be performed or implemented by a computer using commercially available software. Commercially available software of use for performing PLS-DA of NIR absorbance spectra include without limitation, e.g., R and R-Studio (rstudio.com), R-Project (rproject.org), Matlab (mathworks.com), Octave (gnu.org) and NIR Calibration Model (calibrationmodel.com). Additional methods and models for PLS-DA of NIR absorbance spectra that can find use are described, e.g., in Hu, et al., *Talanta* 94 (2012) 301-307; Reeves and Delwiche, J. Near Infrared Spectrosc. (2008) 16:31-38. In varying embodiments, the Monte Carlo method can be applied to PLS-DA (e.g., MC-PLS-DA). See, e.g., So, et al., *Med Eng Phys*. (2013) February; 35(2):172-7. In varying embodiments, Kernel Partial Least Squares for Nonlinear Regression and Discrimination (KPLS) can be applied. See, e.g., Rosipal, Neural Network World, (2003) 13(3):291-300 and Rosipal, et al., *The Journal of Machine Learning Research*, (2002) 2:97-123.

Performing the PLS-DA of the absorbance NIR spectra within the wavelengths evaluated, identifies a value in arbitrary units.

e. Identifying Nuts Having Concealed Damage

Nuts are identified as having concealed damage when the value (in arbitrary units) of the PLS-DA is above a threshold value. Conversely, nuts are identified as not having concealed damage when the value (in arbitrary units) of the PLS-DA is below a threshold value. In varying embodiments, the threshold value is 0.5 (arbitrary units), but in certain embodiments, the threshold value is set at any value between 0.3 and 1.0, e.g., at 0.3, 0.4, 0.5, 0.6, 0.7, 0.8, 0.9 or 1.0 (arbitrary units).

In some embodiments, the methods comprise the further step of separating nuts identified as having concealed damage from nuts identified as not having concealed damage.

3. Systems for Identifying Concealed Damage Nuts

Further provided are systems that carry out or perform the non-destructive methods for identifying nuts having concealed damage, as described above and herein. In varying embodiments, the systems for high throughput evaluation of larger samples of nuts have (i) a conveyor belt; (ii) one or more near infrared (NIR) scanners downstream of a loading point on the conveyor belt and in mechanical communication with the conveyor belt, wherein the one or more NIR scanners are positioned above the conveyor belt and at a proximity and angle to the conveyor belt such that the NIR scanner can scan nuts placed on the conveyor belt; (iii) a computer in communication (e.g., electrical and/or wireless) with the one or more NIR scanners, wherein the computer is capable of performing or implementing one or more steps in the methods described above and herein; and (iv) a deflector in communication (e.g., electrical and/or wireless) with the computer, and optionally in communication (e.g., electrical and/or wireless) with the NIR scanner, wherein the deflector separates nuts identified as having concealed damage from undamaged nuts. In varying embodiments, the high throughput systems can scan and evaluate at least 40 nuts per second.

Systems for evaluating smaller numbers of nuts may operate without the need of a conveyor belt, or even a deflector. Accordingly, in varying embodiments, the systems for high throughput evaluation of larger samples of nuts have (i) a stationary platform; (ii) a movable element attached to a near infrared (NIR) scanner positioned above the stationary platform, wherein the NIR scanner is positioned at a proximity and angle to the platform such that the NIR scanner can scan nuts placed on the platform; and (iii) a computer in communication with the NIR scanner, wherein the computer is capable of performing or implementing one or more steps in the methods described above and herein.

As appropriate, the NIR scanner can be positioned above the conveyor belt or stationary platform at a distance and an angle that allows the accurate NIR scanning of individual nuts on the conveyor belt or stationary platform. The conveyor belt can be of a width sufficient to transport one or more nuts concurrently under the NIR scanner. In varying embodiments, the conveyor belt is of a width in the range of about 2 to 24 inches, e.g., about 2, 3, 4, 5, 6, 7, 8, 9, 10, 11, 12, 13, 14, 15, 16, 17, 18, 19, 20, 21, 22, 23, 24 inches. The deflector mechanically guides the nuts to a collection point (e.g., a bin) based on whether the nut is determined to have concealed damage or not to have concealed damage. The system may further comprise one or more input chutes upstream of a loading point on the conveyor belt and two or more output chutes downstream of the NIR scanner.

Nut sorting machines, equipment and systems are commercially available and can be adapted for implementation of the present methods. Illustrative nut sorting machines are available from Hunter Lab (hunterlab.com), Arecaz Electronics (amirthaasorters.net), Anhui Bida Optoelectronic Technology Co., Ltd. (bidasorter.com), Tomra (tomra.com), Veterans Sorting Machines Private Limited (colorsortingmachines.in) and Buhler Group (buhlergroup.com).

EXAMPLES

The following examples are offered to illustrate, but not to limit the claimed invention.

Example 1

Use of Near-Infrared Spectroscopy and Chemometrics for the Non-Destructive Identification of Concealed Damage in Raw Almonds (*Prunus Dulcis*)

Materials and Methods

Sample Preparation.

Dehulled raw kernels (100 lbs., var. Nonpareil) were supplied by the Nickels Soil lab (Arbuckle, Calif.) in September 2013. Individual vessels containing ~100 gm were exposed to conditions that produced an internal kernel moisture of 5% (actual 5.4±0.2), 8% (actual 8.6±0.7) or 11% (actual 10.4±1.5) in a controlled atmosphere (Thermo Scientific, Marietta, Ohio) at 45±2° C. Under these conditions, CD is observed after 24 hours. The moisture content of the almonds was validated gravimetrically by drying samples (~1 g) at 95-105° C. under vacuum to a constant weight. Moisture was determined in triplicate, and the results were averaged.

Near-Infrared Reflectance Spectra Measurement.

NIR diffuse reflectance spectra were measured on single whole raw almond kernels using an extended MicroNIR 2200 spectrometer (JDSU, USA). The spectral range was collected from 1125-2153 nm using sampling intervals of 8 nm per pixel. The detector used was a 128 pixel uncooled element InGaAs (JDSU, USA). Reflectance spectra data (R) were converted to absorbance using the log (1/R) transformation. A Spectralon® SRM-99 Diffuse Reflectance Standard (Labsphere®, New Hampshire, USA) was used as white calibration reference. For each spectrum, 1000 scans with an integration time of 550 µs were averaged.

Data Pre-Processing.

NIR spectra are complex with broad overlapping NIR absorption bands making it often difficult to identify unique spectral features related to individual chemical components within a given sample. Therefore, a mathematical treatment (pre-processing) of NIR spectra is often used to correct for unwanted systematic sample-to-sample variation (e.g., kernel shape, roughness of kernel surface); help remove spectral baseline shift and scattering caused by particle size differences; reduce band overlapping; and enhance spectral differences (22). Data pre-processing results in relevant NIR spectral data extraction without losing information while removing unwanted information (e.g., interferences or noise) (22).

After the acquisition, NIR spectra were converted to absorbance and pre-processed using either standard normal variate (SNV) or a 9-point second order Savitzky-Golay filter (second derivative preprocessing). These two techniques alone and a combination were compared to determine their effectiveness at removing baseline offsets. Data pre-processing was performed using R and R-Studio (version 0.98.1102). The following packages were used for preprocessing and PLS-DA: ChemometricsWithR (23), signal (24), plyr (25), dplyr (26) and caret (27).

Determination of CD by Colorimetry.

After NIR spectra were acquired, the almonds were roasted at 120° C. for 90 min in a convection oven (Thermo Scientific, USA). Almonds were then split in half along the natural seam and the color of the internal kernel was measured using a ColorFlex colorimeter (HunterLab, USA) according to methods established previously (8). The color values $L^*$ (lightness), C (Chroma), and h (hue), according to the CIE LCh color scale were recorded using a portsize of 0.4 inches with D65 optical sensor, 0° geometry and 10° angle of vision. Almonds with CD ($L^* \leq 71$) were identified and grouped separately from those with no concealed damage (NCD; $L^* > 71$) (8).

Prediction of almonds with concealed damage.

Pre-processed spectra (SNV, second derivative and a combination of both) were analyzed using partial least squares discriminant analysis (PLS-DA). Almonds were separated into two groups (NCD and CD) using colorimetry. The data set (855 almonds) was then randomly divided into a calibration (655 almonds) and a validation (200 almonds) sample set. NCD and CD almonds were assigned constant values of 0 and 1 for a two-class model, respectively.

For the calibration model, repeated cross-validation was used to find the best model. Calibration models were evaluated based on the percentage false positive (% fp), percentage false negative (% fn) and percentage error rate (% ER). A fn was defined as the percentage of NCD almonds classified as those with CD, while fp was defined as CD almonds classified as NCD. The % ER represents the percentage of total almonds incorrectly classified by the predictive method (4, 12).

Results and Discussion

Figure 3:
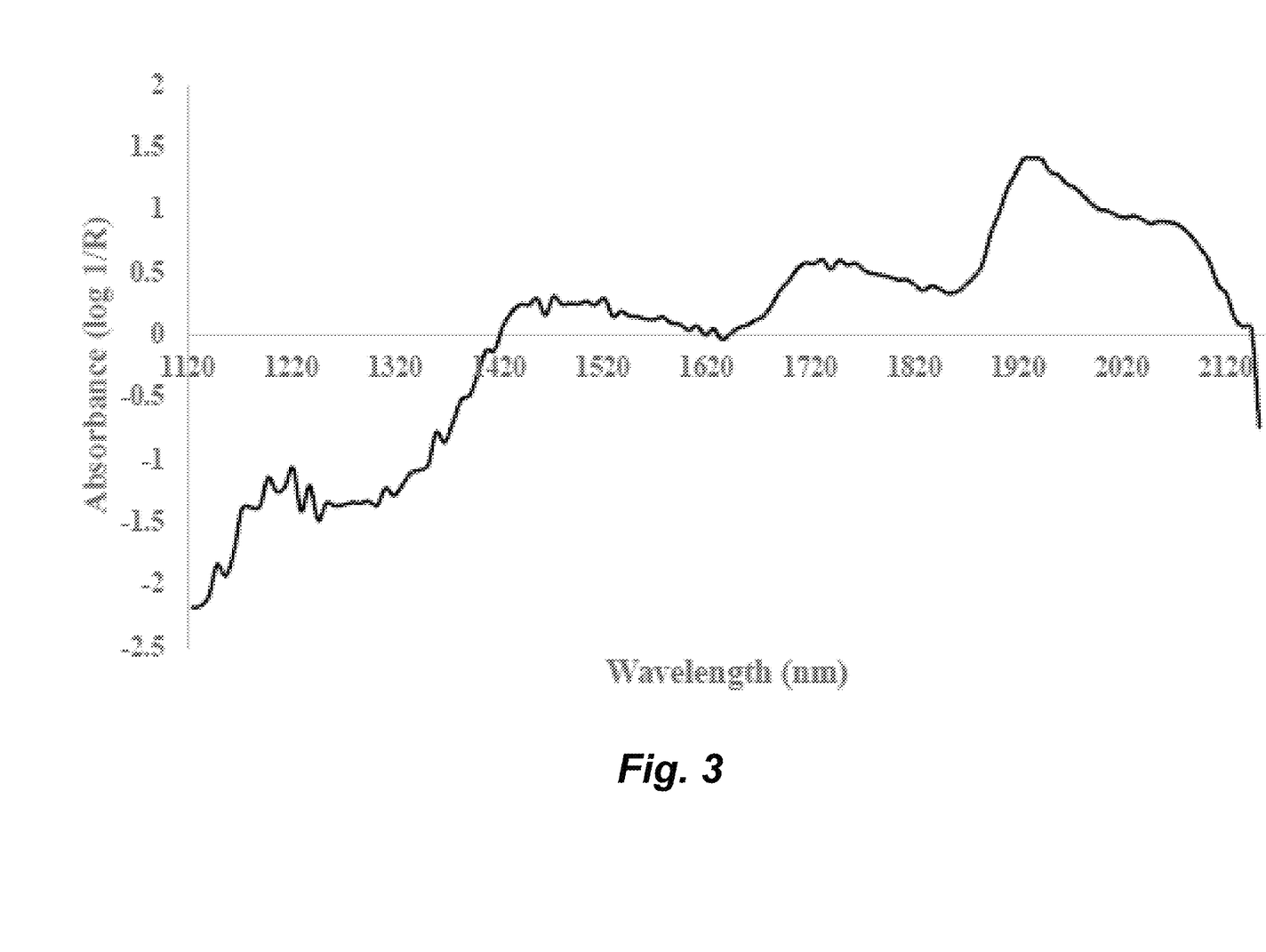
FIG. 3 illustrates the mean standard normal variate (SNV) pre-processed absorbance spectra of almonds with no concealed damage (NCD).
Figure 4:
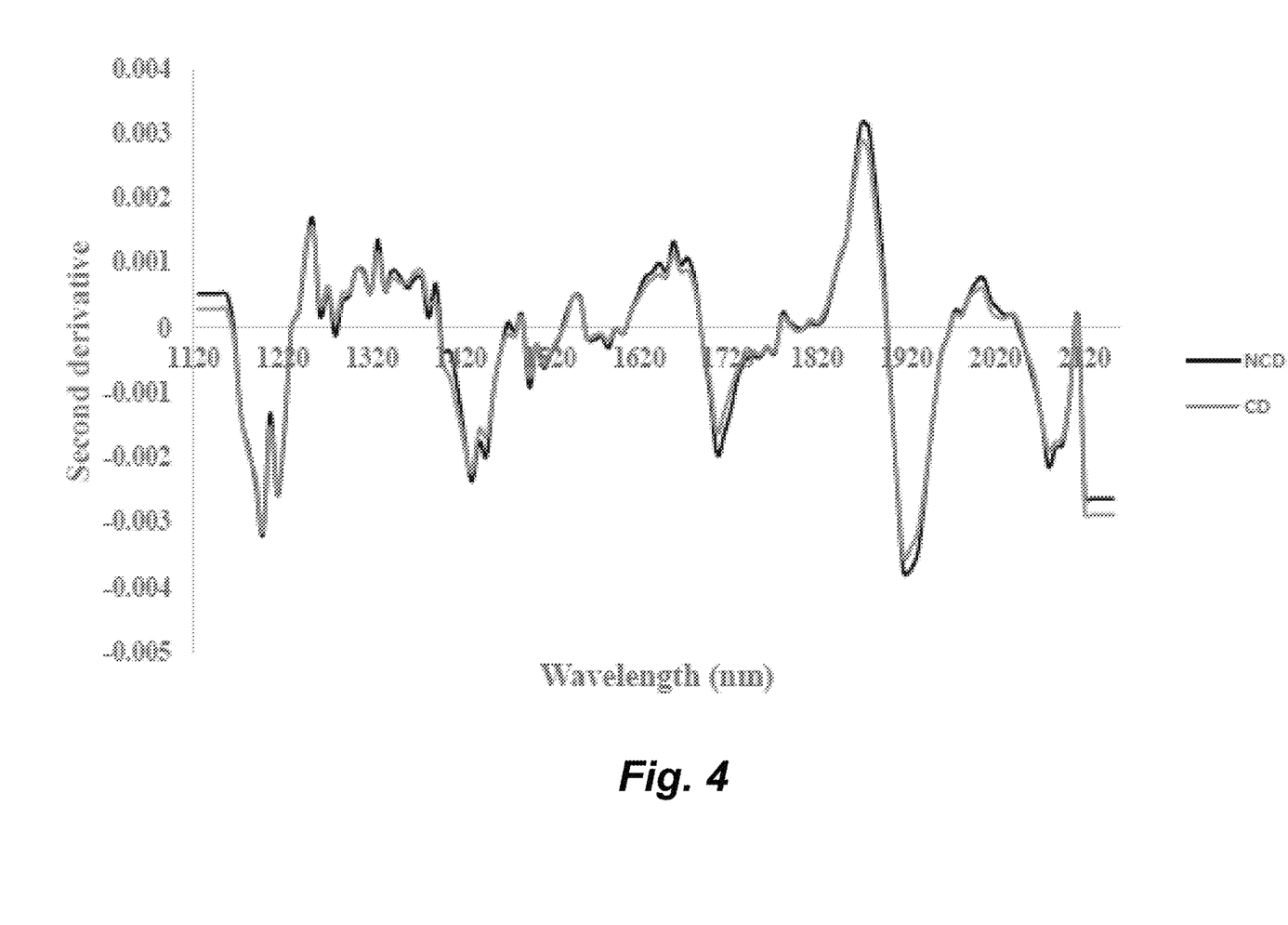
FIG. 4 illustrates a comparison of the mean second derivative (Savitzky-Golay, 9-smoothing points) pre-processed spectra of almonds with no concealed damage (NCD) and with concealed damage (CD).
Figure 5:
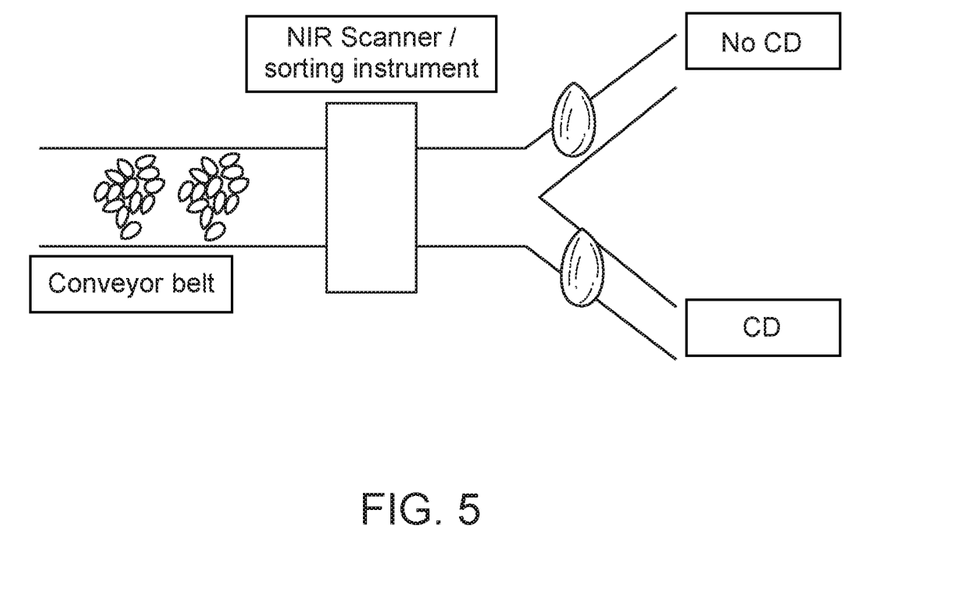
FIG. 5 illustrates a system for identifying and separating out almonds with concealed damage by employing near infrared scanning, as described herein.

A representative NIR spectra (1125-2153 nm) of the NCD almonds, after SNV pre-processing, is shown in FIG. 3. The spectrum is characterized by broad and unresolved absorption bands and is similar to spectra for peanut (28), walnut (10), macadamia nut (7), and shea nut (18). To enhance spectral features and compensate for baseline offsets, a second-derivative of the absorbance data, with respect to wavelength, was calculated. In the second-derivative data, absorbance maxima are converted to minima (FIG. 4). The NIR spectra obtained after applying the second-derivative were characterized by 10 absorption bands. These bands correlate with the major constituents of raw almonds: lipid (50%), carbohydrates (~22%), and protein (~21%) (29). The absorption bands between 1165-1238 nm, 1692-1740 nm and 2064-2104 nm are associated with lipids. These include the C—H (—CH) second overtone stretching band (1200-1214 nm) (30), the C—H (—CH2) first overtone stretching band (1700-1724 nm) (6, 31) and C—H combination band (2098 nm) (32) The absorption bands in between 1408-1462 nm and 1902-1959 nm are associated with the H—OH second overtone of water (18) as well with protein. The absorption bands between 1692-1740 nm and 2064-2104 nm are associated with the absorption of protein (~1700-1850 nm) and amino acids (2080 nm) respectively (32) and the region between 1902-1959 nm correlate to water and amides (~1910-1920 nm) (32). Additionally, the absorption band between 2064-2104 nm can be associated with the O—H and the carboxylic group (C=O—O) band of carbohydrates (31).

An overlay of the averaged second derivative spectra for almonds classified as NCD and CD is also given in FIG. 4. The main differences between the NCD and CD spectra occur at 1432, 1457, 1505, 1513, 1708, 1918 and 2080, 2096 nm. The absorption bands at 1432, 1457, 1505, 1513, and 1918 nm correspond to protein (33), the band at 1708 nm corresponds to free fatty acids and oil (12, 33), and absorption at 2080 and 2096 nm correspond to carbohydrates. Almonds with CD present less absorbance in these regions indicating that kernels display decreased levels of lipids, protein and carbohydrates as compared to controls. These results corresponds to observations of King et al. (1983) (34) who reported that almonds with CD have lower crude fat (oil) and total carbohydrates as compared to almonds with no concealed damage. Additionally, we recently demonstrated higher levels of volatiles related to lipid oxidation and amino acid degradation in almonds with CD as compared to almonds with no concealed damage (8). Taken together these results indicate the metabolic processes that activate the degradation of proteins, carbohydrates and lipids are involved in the development of CD. The free amino acids, sugars and products from the oxidation of lipids would be substrates for the Maillard reaction and supports the hypothesis that the Maillard reaction is involved in the formation of CD in almonds.

Initially, multiple PLS-DA models were evaluated using the full wavelength region from 1125-2153 nm after data pre-processing (SNV, second derivative, and SNV and the second derivative). In general, the best predictive models give low percentage error rates (i.e. the highest percentage of correct classification). Herein we found that using the full wavelength region resulted in models with high percentage error rates and therefore PLS-DA models were developed using only relevant portions of the NIR spectra. Table 1 summarize the prediction performance of the calibration models and validation models, which were selected as they had the lowest percent of error (% ER), false positive (% fp) and false negative (% fn) rates. A large data set (200 samples) was analyzed to optimize the prediction models. The lowest % ER (8.2%) was obtained using only second derivative pre-processing as compared to 9.2% when using SNV pre-processing, and 8.2% when using SNV and second derivative pre-processing. Although the % fp rate was higher for this model (17.2%) as compared to the SNV (12.6%) and SNV and second derivative pre-processing (10.6%), the % fn was significantly lower (12.4%) as compared to these models (16%).

TABLE 1

Results Of The PLS-DA Model Using Standard Normal Variate (SNV), Second Derivative, And SNV And Second Derivative Pre-Processing.

|  | SNV | Second derivative | Second derivative + SNV |
|---|---|---|---|
| a) Calibration Model | | | |
| Wavelength selected (nm) | 1408-1465 | 1408-1465 | 1408-1465 |
|  | 1902-1959 | 1692-1740 | 1692-1740 |
|  |  | 1902-1959 | 1902-1959 |
|  |  | 2064-2104 |  |
| # Latent variables | 4 | 7 | 4 |
| ROC*/% Error rate | 0.908/9.2 | 0.918/8.2 | 0.918/8.2 |
| Specificity/% fn | 0.839/16.1 | 0.876/12.4 | 0.840/16.0 |
| Selectivity/% fp | 0.874/12.6 | 0.828/17.2 | 0.894/10.6 |
| b) Validation Model | | | |
| % Error rate | 9 | 7 | 9 |
| % false positive (% fp) | 8 | 8 | 9 |
| % false negative (% fn) | 11 | 6 | 7 |

*Area under the Receiver Operating Characteristics

Previous studies employing IR to build models to discriminate differences between CD and NCD focused on the absorbance range between 700-1400 nm (5) and on selected wavelengths within the 700-1400 nm absorbance range (20-21) Comparisons of these results with results obtained herein are summarized in Table 2. Although the % fp were lower across these studies (0.7-5.4%), as compared with our results (12.4-16.1%), the rate of % fn were significantly higher (11.1-62.96%) than those obtained using our predictive models (10.6-17.2%). Additionally, the % ER ranged from 5.8-27.5% whereas our predictive models gave a much narrower range of 8.2-9.2%. The three PLS-DA models presented herein offer significant improvements in the prediction capabilities and are able to identify almonds with CD with 90.8-91.8% certainty based upon calibration models. Although any of the three models presented could be considered for further development of a rapid in-line screening method for detecting CD in raw almonds, the PLS-DA model based on the second derivative spectra and utilizing four wavelength ranges (e.g., 1408-1462, 1692-1740, 1902-1959 and 2064-2104 nm) gives the lowest rate of false negatives and may be the best choice for further method development.

TABLE 2

Comparison Of NIR Validation Results Between Methods Used In The Classification Of Almond With Concealed Damage (CD).

|  | Pearson, T.C (1998) | Nakariyakul, S. (2014) | Nakariyakul et al. (2011) | Results Obtained Herein* |
|---|---|---|---|---|
| Range (nm) | 700-1400 | 700-1400 (selected wavelength) | 700-1400 (selected wavelength) | 1125-2153 (selected wavelength) |
| % Error rate | 12.4-27.5 | 5.8 | 8.8 | 8.2-9.2 |
| % False positive | 0.7-5.4 | 2.91-3.41 | 0.58-1.74 | 12.4-16.1 |
| % False negative | 11.1-23.8 | 14.81-62.96 | 31.48-53.70 | 10.6-17.2 |

*Based on calibration models

Our results indicate that these PLS-DA predictive models offer advantages over previously reported models and that CD is related to the degradation of lipids, carbohydrates and proteins in almonds.

REFERENCES FOR BACKGROUND AND EXAMPLE 1

(1) Reil, W, J. M. Labavitch, D. Holmberg. 1996. Harvesting. In Almond Production Manual. W. C. Micke, editor. University of California, Division of Agriculture and Natural Resources (publication 3364). Oakland, Calif. pp. 260-264.
(2) Kader, A. A. and J. F. Thompson. 1992. Postharvest handling systems: Tree nuts in Postharvest Technology of Horticultural Crops. A. A. Kader, editor. University of California, Division of Agriculture and Natural Resources, publication 3311. pp. 254.
(3) Halbrook, W. U; Fuller, G.; Whitehand, L. C. Almond Nutmeat Moisture and Water Activity and its Influence on Fungal Flora and Seed Composition. J. Food Sci. 1983, 48, 615-617.
(4) Pearson, T. C. Spectral Properties and Effect of Drying Temperature on Almonds with Concealed Damage. LWT—Food Sci. Technol. 1999, 32, 67-72.
(5) Pannico, A.; Schouten, R. E.; Basile, B.; Romano, R.; Woltering, E. J.; Cirillo, C. Non-destructive detection of flawed hazelnut kernels and lipid oxidation assessment using NIR spectroscopy. J. Food Eng. 2015, 160, 42-48.
(6) Huang, H.; Yu, H.; Xu, H.; Ying, Y. Near infrared spectroscopy for on/in-line monitoring of quality in foods and beverages: A review. J. Food Eng. 2008, 87, 303-313.
(7) Guthrie, J.; Greensill, C.; Bowden, R.; Walsh, K. Assessment of quality defects in macadamia kernels using NIR spectroscopy. Aust. J. Agric. Res. 2004, 55, 471-476.
(8) Rogel-Castillo, C.; Zuskov, D.; Chan, B. L.; Lee, J.; Hong, G.; Mitchell, A. E. Effect of Temperature and Moisture on the Development of Concealed Damage in Raw Almonds (*Prunus dulcis*). J Agric Food Chem. 2015, 63, 8234-8240.
(9) Buning-Pfaue, H. Analysis of water in food by near infrared spectroscopy. Food Chemistry. 2003, 82, 107-115.
(10) Jensen, P. N.; Sorensen, G.; Engelsen, S. B.; Bertelsen, G. Evaluation of Quality Changes in Walnut Kernels (*Juglans regia* L.) by Vis/NIR Spectroscopy. J. Agric. Food Chem. 2001, 49, 5790-5796.
(11) Liu, J.; Li, X. Y.; Li, P. W.; Wang, W.; Zhang, J.; Zhang, R.; Liu, P. Nondestructive detection of moldy chestnut based on near infrared spectroscopy. Afr. J. Agric. Res. 2010, 5, 3213-3218.

(12) Moscetti, R.; Haff, R. P.; Saranwong, S.; Monarca, D.; Cecchini, M.; Massantini, R. Nondestructive detection of insect infested chestnuts based on NIR spectroscopy. Postharvest Biol. Technol. 2014, 87, 88-94.

(13) Moscetti, R.; Haff, R. P.; Aernouts, B.; Saeys, W.; Monarca, D.; Cecchini, M.; Massantini, R. Feasibility of Vis/NIR spectroscopy for detection of flaws in hazelnut kernels. J. Food Eng. 2013, 118, 1-7.

(14) Pannico, A.; Schouten, R. E.; Basile, B.; Romano, R.; Woltering, E. J.; Cirillo, C. Non-destructive detection of flawed hazelnut kernels and lipid oxidation assessment using NIR spectroscopy. J. Food Eng. 2015, 160, 42-48.

(15) Wang, D.; Dowell, F.; Ram, M.; Schapaugh, W., Classification of fungal-damaged soybean seeds using near-infrared spectroscopy. Int. J. Food Prop. 2004, 7, 75-82.

(16) Tillman, B. L.; Gorbet, D. W.; Person, G. Predicting Oleic and Linoleic Acid Content of Single Peanut Seeds using Near-Infrared Reflectance Spectroscopy. Crop Sci. 2006, 46, 2121-2126.

(17) Bellincontro, A.; Fracas, A.; DiNatale, C.; Esposito, G.; Anelli, G.; Mencarelli, F. Use of NIR Technique to Measure the Acidity and Water Content of Hazelnuts. Acta Hortic. 2005, 686, 499-503.

(18) Davrieux, F.; Allal, F.; Piombo, G.; Kelly, B.; Okulo, J. B.; Thiam, M.; Diallo, 0. B.; Bouvet, J. M. Near infrared spectroscopy for high-throughput characterization of Shea tree (*Vitellaria paradoxa*) nut fat profiles. J Agric Food Chem. 2010, 58, 7811-7819.

(19) Pearson, T. C., Use of near infrared transmittance to automatically detect almonds with concealed damage. LWT—Food Sci. Technol. 1999, 32, 73-78.

(20) Nakariyakul, S., Internal damage inspection of almond nuts using optimal near-infrared waveband selection technique. J. Food Eng. 2014, 126, 173-177.

(21) Nakariyakul, S.; Casasent, D. P. Classification of internally damaged almond nuts using hyperspectral imagery. J. Food Eng. 2011, 103, 62-67.

(22) Metrohm NIRSystem. Herisau, Switzerland. Monograph: NIR Spectroscopy A guide to near-infrared spectroscopic analysis of industrial manufacturing processes. Retrieved Apr. 16, 2016 from: http://www.mep.net.au/wpmep/wp-content/uploads/2013/05/MEP_Monograph_NIRS_81085026EN.pdf (23) Wehrens, R. Chemometrics With R: Multivariate Data Analysis in the Natural Sciences and Life Sciences. 2011, Springer, Heidelberg.

(24) Signal developers. signal: Signal processing. 2015. URL: http://r-forge.r-project.org/projects/signal/.

(25) Wickham, H. The Split-Apply-Combine Strategy for Data Analysis. J. Stat. Softw. 2011. 40, 1-29. URL http://www.jstatsoft.org/v40/i01/.

(26) Wickham, H.; Francois, R. dplyr: A Grammar of Data Manipulation. R package version 0.4.3. 2015. https://CRAN.R-project.org/package=dplyr (27) Kuhn, M.; Wing, J.; Weston, S.; Williams, A.; Keefer, C.; Engelhardt, A.; Cooper, T.; Mayer, Z.; Kenkel, B.; Benesty, M.; Lescarbeau, R.; Ziem, A.; Scrucca, L.; Tang, Y.; Candan, C. caret: Classification and Regression Training. R package version 6.0-68. 2016. https://CRAN.R-project.org/package=caret (28) Govindarajan, K. N.; Kandala, C. V. K.; Subbiah, J. NIR Reflectance Spectroscopy for Nondestructive Moisture Content Determination in Peanut Kernels. Trans. ASABE. 2009, 52, 1661-1665.

(29) (USDA) US Department of Agriculture, Agricultural Research Service, 2015. USDA National Nutrient Database for Standard Reference, Release 27. Retrieved Aug. 26, 2015 from: Nutrient Data Laboratory Home Page: http://ndb.nal.usda.gov/ndb/search (30) Sathe, S.; Seeram, N.; Kshirsagar, H.; Heber, D.; Lapsley, K. Fatty acid composition of California grown almonds. J. Food Sci. 2008, 73, C607-C614.

(31) Moscetti, R.; Monarca, D.; Cecchini, M.; Haff, R. P.; Contini, M.; Massantini, R., Detection of Mold-Damaged Chestnuts by Near-Infrared Spectroscopy. Postharvest Biol. Technol. 2014, 93, 83-90.

(32) Fassio, A.; Cozzolino, D. Non-destructive prediction of chemical composition in sunflower seeds by near infrared spectroscopy. Ind. Crops Prod. 2004, 20, 321-329.

(33) Workman Jr, J.; Weyer, L., Appendix D. Spectra— Structure Correlations for Near Infrared. In Practical guide and spectral atlas for interpretive near-infrared spectroscopy, Second edition; CRC Press: 2012; pp 229-267.

(34) King Jr., A. D.; Halbrook, W. U.; Fuller, G.; Whitehand, L. C. Almond Nutmeat Moisture and Water Activity and its Influence on Fungal Flora and Seed Composition. J. Food Sci. 1983, 48, 615-617.

Example 2

Use of Near-Infrared Spectroscopy for the Non-Destructive Identification of Concealed Damage in Raw Almonds (*Prunus Dulcis*)

Materials and Methods

This example demonstrates the identification of concealed damage in raw almonds employing smoothing and second derivative preprocessing.

Sample preparation. Dehulled raw kernels (50 lbs., var. Nonpareil) were supplied by Baldwin Minkler Farms (Orland, Calif.) in May 2015. For every drying condition, two vessels each containing one hundred almond kernels were exposed to moisture in a controlled atmosphere incubator (Thermo Scientific, Marietta, Ohio) at 45±2° C. for 24 hours to induce the development of CD (Rogel-Castillo, et al., *Journal of Agricultural and Food Chemistry*, (2015) 63(37), 8234-8240, hereby incorporated herein by reference in its entirety). Then the individual vessels were removed from the oven dried at several temperatures: 45° C., 55° C., 65° C., 75° C., 85° C. and 95° C. to a final moisture of 5-6%.

Near-infrared reflectance spectra measurement. NIR diffuse reflectance spectra were measured on single whole raw almond kernels using an extended MicroNIR 2200 spectrometer (JDSU, USA). The spectral range was collected from 1125-2153 nm using sampling intervals of 8 nm per pixel. The detector used was a 128 pixel uncooled element InGaAs (JDSU, USA). Reflectance spectra data (R) were converted to absorbance using the log (1/R) transformation. A Spectralon® SRM-99 Diffuse Reflectance Standard (Labsphere®, New Hampshire, USA) was used as white calibration reference. For each spectrum, 30 scans with an integration time of 2500 μs were averaged.

Data Pre-Processing.

After the acquisition, NIR spectra were converted to absorbance and pre-processed using smoothing with a 15-point second order Savitzky-Golay filter (second derivative preprocessing). Data pre-processing was performed using R and R-Studio (version 0.98.1102).

Prediction of Almonds with Concealed Damage.

Pre-processed spectra (smoothing and second derivative) were analyzed using partial least squares discriminant analysis (PLS-DA). Almonds were separated into two groups (NCD and CD) using colorimetry. The data set (1,544 almonds) was then randomly divided into a calibration (1,158 almonds) and a validation (386 almonds) sample set. NCD and CD almonds were assigned constant values of 0 and 1 for a two-class model, respectively.

Predictive model was evaluated based on the percentage false positive (% fp), percentage false negative (% fn) and percentage error rate (% ER). A fn was defined as the percentage of NCD almonds classified as those with CD, while fp was defined as CD almonds classified as NCD. The % ER represents the percentage of total almonds incorrectly classified by the predictive method.

Results

Validation results of the PLS-DA classification model using smoothing and second derivative pre-processing and selected wavelength (1392-1546 nm; 1692-1781 nm; 1902-1991 nm) is summarized in Table 3.

TABLE 3

| Preprocess | Classification method | Calibration data set | | | Validation data set | | |
|---|---|---|---|---|---|---|---|
| | | % Error rate | % False positive | % False negative | % Error rate | % False positive | % False negative |
| Smooth - $2^{nd}$ order* | PLS-DA (36 comp) | 18 | 21 | 30 | 19 | 16 | 25 |

TABLE 4

| % CD predicted using an external data set | | |
|---|---|---|
| | Observed | Predicted |
| Control (No moisture damage) | 4 | 23 |
| CD (Moisture damage) | 96 | 87 |

REFERENCES

Luypaert, J., Zhang, M. H., & Massart, D. L. (2003). Feasibility study for the use of near infrared spectroscopy in the qualitative and quantitative analysis of green tea, *Camellia sinensis* (L.). Analytica Chimica Acta, 478(2), 303-312.

Cen, H., & He, Y. (2007). Theory and application of near infrared reflectance spectroscopy in determination of food quality. Trends in Food Science & Technology, 18(2), 72-83.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying a nut having concealed damage, the method comprising the steps of:
   a) obtaining Near-Infrared Spectroscopy (NIR) diffuse reflectance spectra between 1125-2153 nm of a dehulled whole raw nut;
   b) converting the NIR reflectance spectra to NIR absorbance spectra;
   c) extracting the NIR absorbance spectra within the wavelength ranges of 1392-1546 nm, 1692-1781 nm, and 1902-1991 nm from the NIR absorbance spectra;
   d) evaluating the NIR absorbance spectra only within the wavelength ranges of 1392-1546 nm, 1692-1781 nm, and 1902-1991 nm;
   e) performing partial least square discriminant analysis (PLS-DA) within the wavelength ranges of step d) and assigning a PLS-DA value; and
   f) identifying the nut as having concealed damage when the PLS-DA value is above a threshold value.

2. The method of claim 1, wherein the NIR absorbance spectra are subject to Standard Normal Variate (SNV) pre-processing.

3. The method of claim 1, wherein the NIR absorbance spectra are subject to second order Savitzky-Golay filter or second derivative preprocessing.

4. The method of claim 1, wherein the NIR absorbance spectra are subject to combination of (i) second order Savitzky-Golay filter or second derivative preprocessing and (ii) Standard Normal Variate (SNV) preprocessing.

5. The method of claim 4, wherein the preprocessing employs a 9 point second order Savitzky-Golay filter.

6. The method of claim 1, wherein the NIR absorbance spectra are subject to (i) smoothing preprocessing and (ii) second order Savitzky-Golay filter or second derivative preprocessing.

7. The method of claim 6, wherein the preprocessing employs a 15 point second order Savitzky-Golay filter.

8. The method of claim 1, wherein the converting step (b) employs log (1/R) transformation.

9. The method of claim 1, wherein the nut is selected from the group consisting of almonds, pistachios, pecans, walnuts, shea nuts, macadamia nuts, hazel nuts, peanuts, cashews, walnuts, chestnuts, pine nuts and brazil nuts.

10. The method of claim 1, wherein one or more of the steps of the method are automated.

11. The method of claim 1, further comprising the step g) of separating nuts identified as having concealed damage from nuts identified as not having concealed damage.

12. The method of claim 1, wherein one or more of steps a) to g) are performed or implemented by a computer.

13. The method of claim 1, wherein the dehulled whole raw nut is not purposefully breached, split or damaged.

14. The method of claim 1, wherein the whole dehulled raw nut is not subject to a heat treatment.

15. The method of claim 14, wherein the nut is not subject to heat treatment, blanched, or roasted.

16. The method of claim 1, wherein for each spectrum, 30-1000 scans with an integration time of 550-2500 µs are averaged.

17. The method of claim 1, wherein the method has an overall error rate of less than about 10% and a false negative error rate of less than about 20%.

18. A system for identifying a nut having concealed damage, the system comprising:
   (i) a conveyor belt;
   (ii) one or more near infrared (NIR) scanners downstream of a loading point on the conveyor belt and in mechanical communication with the conveyor belt, wherein the one or more NIR scanners are positioned above the conveyor belt and at a proximity and angle to the conveyor belt such that the one or more NIR scanners can scan nuts placed on the conveyor belt;

(iii) a computer in communication with the one or more NIR scanners, wherein the computer is configured to perform or implement the following steps:

a) obtaining Near-Infrared Spectroscopy (NIR) diffuse reflectance spectra between 1125-2153 nm of a dehulled whole raw nut;

b) converting the NIR reflectance spectra to NIR absorbance spectra;

c) extracting the NIR absorbance spectra within the wavelength ranges of 1392-1546 nm, 1692-1781 nm, and 1902-1991 nm from the NIR absorbance spectra;

d) evaluating the NIR absorbance spectra only within the wavelength ranges of 1392-1546 nm, 1692-1781 nm, and 1902-1991 nm;

e) performing partial least square discriminant analysis (PLS-DA) within the wavelength ranges of step d) and assigning a PLS-DA value; and f) identifying the nut as having concealed damage when the PLS-DA value is above a threshold value;

(iv) a deflector in communication with the computer, and in communication with the one or more NIR scanners, wherein the deflector separates nuts identified as having concealed damage from undamaged nuts.

19. A system for identifying a nut having concealed damage, the system comprising:

(i) a stationary platform;

(ii) a movable element attached to a near infrared (NIR) scanner positioned above the stationary platform, wherein the NIR scanner is positioned at a proximity and angle to the stationary platform such that the NIR scanner can scan nuts placed on the stationary platform; and (iii) a computer in communication with the NIR scanner, wherein the computer is capable of performing or implementing one or more the steps in the method of claim 1.

* * * * *